United States Patent
Moinard et al.

(10) Patent No.: US 11,419,838 B2
(45) Date of Patent: Aug. 23, 2022

(54) COMPOSITIONS COMPRISING CITRULLINE AND LEUCINE AND THEIR USE IN THE TREATMENT OF DIABETES AND METABOLIC SYNDROME

(71) Applicant: NESTEC S.A., Vevey (CH)

(72) Inventors: Christophe Moinard, Bourg la Reine (FR); Gabrielle Ventura, Paris (FR); Denis Breuille, Lausanne (CH); Christian Darimont-Nicolau, Lausanne (CH); Luc Cynober, Sceaux (FR)

(73) Assignee: Societe des Produits Nestle S.A., Vevey (CH)

(*) Notice: Subject to any disclaimer, the term of this patent is extended or adjusted under 35 U.S.C. 154(b) by 277 days.

(21) Appl. No.: 15/892,078

(22) Filed: Feb. 8, 2018

(65) Prior Publication Data

US 2018/0338942 A1 Nov. 29, 2018

Related U.S. Application Data

(62) Division of application No. 15/027,580, filed as application No. PCT/EP2014/071230 on Oct. 3, 2014, now Pat. No. 9,913,818.

(60) Provisional application No. 61/888,636, filed on Oct. 9, 2013.

(51) Int. Cl.
*A61K 31/198* (2006.01)
*A61K 31/16* (2006.01)
*A61K 31/17* (2006.01)
*A61K 45/06* (2006.01)

(52) U.S. Cl.
CPC ............ *A61K 31/198* (2013.01); *A61K 31/16* (2013.01); *A61K 31/17* (2013.01); *A61K 45/06* (2013.01)

(58) Field of Classification Search
CPC ....... A61K 31/198; A61K 31/16; A61K 31/17
See application file for complete search history.

(56) References Cited

U.S. PATENT DOCUMENTS 8,017,657 B1 * 9/2011 Petrus ................. A61K 9/0056
424/465
2013/0017283 A1 1/2013 Zemel et al.

FOREIGN PATENT DOCUMENTS

| EP | 2647374 | 10/2013 |
|---|---|---|
| WO | 0249636 | 6/2002 |
| WO | 2012005568 | 1/2012 |
| WO | 2012143403 | 10/2012 |
| WO | 2013120022 | 8/2013 |

OTHER PUBLICATIONS

Zhang et al. "Increasing Dietary Leucine Intake Reduces Diet-Induced Obesity and Improves Glucose and Cholesterol Metabolism in Mice via Multimechanisms" Diabetes, 2007, vol. 56, pp. 1647-1654.
Wu et al. "Dietary Supplementation with Watermelon Pomace Juice Enhances Arginine Availability and Ameliorates the Metabolic Syndrome in Zucker Diabetic Fatty Rats" The Journal of Nutrition, 2007, vol. 137, pp. 2680-2685.
Bastaki "Review: Diabetes Mellitus and its treatment" Int. J. Diabetes Metab., 2005, vol. 13, pp. 111-134.
Annals of internal medicine; vol. 164, No. 8, Apr. 19, 2016.

* cited by examiner

*Primary Examiner* — Pancham Bakshi
(74) *Attorney, Agent, or Firm* — K&L Gates LLP

(57) ABSTRACT

Compositions contain citrulline and leucine or a metabolite thereof including, for example, a synergistic amount of citrulline and leucine. Such compositions may be used in methods for the treatment of pre-diabetes, metabolic syndrome, hyperglycemia, or diabetes.

9 Claims, 1 Drawing Sheet

COMPOSITIONS COMPRISING CITRULLINE AND LEUCINE AND THEIR USE IN THE TREATMENT OF DIABETES AND METABOLIC SYNDROME

PRIORITY CLAIM

The present application is a Divisional of U.S. patent application Ser. No. 15/027,580 filed Apr. 6, 2016, which is a National Stage of International Application No. PCT/EP2014/071230 filed Oct. 3, 2014, which claims priority to U.S. Provisional Patent Application No. 61/888,636 filed Oct. 9, 2013, the entire contents of which are incorporated herein by reference.

BACKGROUND

The present disclosure generally relates to methods and compositions for treatment or prevention of pre-diabetes, diabetes, hyperinsulinemia, hyperglycemia, and metabolic syndrome. More specifically, the present disclosure relates to compositions that comprise a synergistic amount of both citrulline and leucine.

Insulin resistance is associated with a number of disease states and conditions and is present in approximately 30-40% of non-diabetic individuals. These disease states and conditions include, but are not limited to, pre-diabetes and metabolic syndrome (also referred to as insulin resistance syndrome). Pre-diabetes is a state of abnormal glucose tolerance characterized by either impaired glucose tolerance (IGT) or impaired fasting glucose (IFG). Patients with pre-diabetes are insulin resistant and are at high risk for future progression to overt Type 2 diabetes. Metabolic syndrome is an associated cluster of traits that include, but is not limited to, hyperinsulinemia, abnormal glucose tolerance, obesity, redistribution of fat to the abdominal or upper body compartment, hypertension, dysfibrinolysis, and a dyslipidemia characterized by high triglycerides, low HDL-cholesterol, and small dense LDL particles. Insulin resistance has been linked to each of the traits, suggesting metabolic syndrome and insulin resistance are intimately related to one another.

SUMMARY

The present inventors surprisingly and unexpectedly found that administration of citrulline and leucine (or a metabolite thereof) has a synergistic effect and is able to reduce fasting glucose levels and fasting insulin plasma levels below the level of reduction obtained with individual administration of citrulline or leucine.

The present disclosure relates to methods of treating or preventing a disease or condition in a subject in need thereof (e.g., an obese or overweight subject) comprising administering to the subject a therapeutically effective amount of citrulline and a therapeutically effective amount of leucine (or a metabolite thereof). The therapeutically effective amount of citrulline and a therapeutically effective amount of leucine (or a metabolite thereof) may be administered to the subject at the same time or at a different time and may be administered in amounts that have a synergistic effect.

The present disclosure provides methods of treating or preventing a disease or condition in a subject in need thereof comprising administering to the subject a therapeutically effective amount of citrulline and a therapeutically effective amount of leucine (or a metabolite thereof).

In some embodiments, the disease or condition is selected from the group consisting of: pre-diabetes, diabetes, hyperinsulinemia, hyperglycemia, metabolic syndrome, obesity, and combinations thereof.

In an embodiment, the disease or condition is metabolic syndrome.

In another embodiment, the disease or condition is hyperinsulinemia.

In another embodiment, the disease or condition is hyperglycemia.

In another embodiment, the metabolite of leucine is hydroxy isocaproic acid (HICA) or beta-hydroxy-beta-methylbutyrate (HMB).

In another embodiment, the therapeutically effective amount of citrulline and the therapeutically effective amount of leucine (or a metabolite thereof) are present in a synergistic amount.

In another embodiment, citrulline and leucine (or a metabolite thereof) is administered to the subject weekly, daily, two times a day, or three times a day.

In another embodiment, the subject is administered a fixed amount citrulline and leucine (or a metabolite thereof).

In another embodiment, the subject is administered a weight-based dose of citrulline and leucine (or a metabolite thereof).

In another embodiment, the weight-based dose is about 0.01 g/kg to about 0.3 g/kg.

In another embodiment, a pharmaceutical composition is administered to the subject that comprises both the therapeutically effective amount of citrulline and the therapeutically effective amount of leucine (or a metabolite thereof).

In another embodiment, the therapeutically effective amount of citrulline and the therapeutically effective amount of leucine (or a metabolite thereof) are administered orally.

In another embodiment, the method is effective to achieve at least one of the following modifications: reduction in fasting blood sugar level, decrease in insulin resistance, reduction of hypoinsulinemia, improvement in glucose tolerance, or any combination thereof.

In another embodiment, the therapeutically effective amount of citrulline and the therapeutically effective amount of leucine (or a metabolite thereof) is administered in conjunction with at least one additional treatment method, said additional treatment method comprising administering at least one pharmaceutical composition comprising an active agent selected from the group consisting of: a sulfonylurea, a meglitinide, a biguanide, an alpha-glucosidase inhibitor, a thiazolidinedione, a DPP-IV inhibitor, a glucagon-like peptide (GLP)-1 analog, or insulin.

The present disclosure also provides a composition, nutritional composition, or medical food comprising citrulline and leucine (or a metabolite thereof) useful for the treatment of pre-diabetes, diabetes, hyperinsulinemia, hyperglycemia, metabolic syndrome, obesity, or any combination thereof.

In an embodiment, the metabolite of leucine is hydroxy isocaproic acid (HICA) or beta-hydroxy-beta-methylbutyrate (HMB).

In another embodiment, citrulline and leucine are present in a synergistic amount.

In another embodiment, citrulline and leucine are both present in an amount effective to treat metabolic syndrome, hyperglycemia, or hyperinsulinemia.

In another embodiment, the composition is a pharmaceutical composition.

These and other embodiments of the disclosure are described in further detail herein below.

BRIEF DESCRIPTION OF THE FIGURES

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

DETAILED DESCRIPTION

Figure 1:
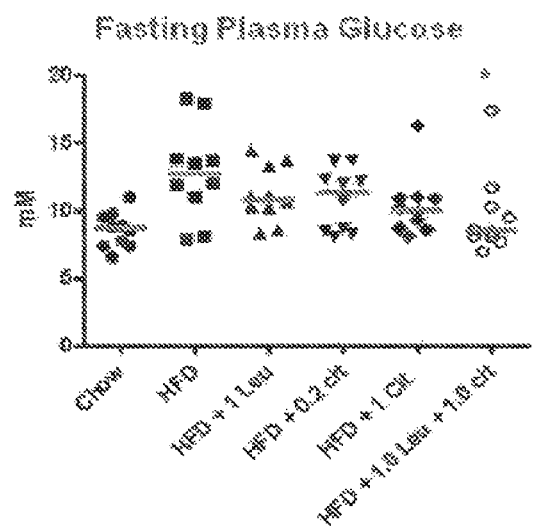
FIG. 1 shows fasting glucose levels in rats fed a high fat diet (HFD) and treated with 0.2 or 1.0 g/kg/day of citrulline, 1.0 g/kg/day of leucine or 1.0 g/kg/day of both citrulline and leucine. P<0.05 versus HFD.

All dosage ranges contained within this application are intended to include all numbers, whole or fractions, contained within said range. All percentages expressed herein are by weight of the total weight of the fiber blend unless expressed otherwise. As used herein, "about" is understood to refer to numbers in a range of numerals. Moreover, all numerical ranges herein should be understood to include all integer, whole or fractions, within the range.

As used herein, "subject" includes, but is not limited to, mammals, which include but is not limited to, rodents, aquatic mammals, domestic animals such as dogs and cats, farm animals such as sheep, pigs, cows and horses, and humans. A subject may include a "patient" which is understood to include an animal, especially a mammal, and more especially a human that is receiving or intended to receive treatment, as treatment is herein defined. While the terms "individual" and "patient" are often used herein to refer to a human, the present disclosure is not so limited. Accordingly, the terms "individual" and "patient" refer to any animal, mammal or human, having or at risk for a medical condition that can benefit from the treatment.

"Nutritional compositions," as used herein, are understood to include any number of optional additional ingredients, including conventional food additives, for example one or more, acidulants, additional thickeners, buffers or agents for pH adjustment, chelating agents, colorants, emulsifies, excipient, flavor agent, mineral, osmotic agents, a pharmaceutically acceptable carrier, preservatives, stabilizers, sugar, sweeteners, texturizers, and/or vitamins. The optional ingredients can be added in any suitable amount.

The terms "prevention", "prevent", "preventing", "suppression", "suppress", "suppressing", "inhibit" and "inhibition" as used herein refer to a course of action (such as administering a compound or pharmaceutical composition) initiated in a manner (e.g., prior to the onset of a clinical symptom of a disease state or condition) so as to prevent, suppress or reduce, either temporarily or permanently, the onset of a clinical manifestation of the disease state or condition. Such preventing, suppressing or reducing need not be absolute to be useful.

The terms "treatment", "treat" and "treating" as used herein refers a course of action (such as administering a compound or pharmaceutical composition) initiated after the onset of a clinical symptom of a disease state or condition so as to eliminate, reduce, suppress or ameliorate, either temporarily or permanently, a clinical manifestation or progression of the disease state or condition. Such treating need not be absolute to be useful.

As used herein, the term "in need of treatment" refers to a judgment made by a caregiver that a patient requires or will benefit from treatment. This judgment is made based on a variety of factors that are in the realm of a caregiver's expertise, but that includes the knowledge that the patient is ill, or will be ill, as the result of a condition that is treatable by a method or compound of the disclosure.

As used herein, the term "in need of prevention" refers to a judgment made by a caregiver that a patient requires or will benefit from prevention. This judgment is made based on a variety of factors that are in the realm of a caregiver's expertise, but that includes the knowledge that the patient will be ill or may become ill, as the result of a condition that is preventable by a method or compound of the disclosure.

As used herein, the term "therapeutically effective amount" refers to an amount of citrulline or leucine (or a metabolite thereof), either alone or as a part of a pharmaceutical composition, that is capable of having any detectable, positive effect on any symptom, aspect, or characteristics of a disease state or condition when administered to a patient (e.g., as one or more doses). Such effect need not be absolute to be beneficial.

The term "insulin resistance" as used herein refers to a condition where a normal amount of insulin is unable to produce a normal physiological or molecular response. In some cases, a hyper-physiological amount of insulin, either endogenously produced or exogenously added, is able to overcome the insulin resistance in whole or in part and produce a biologic response.

Methods of treating or preventing a disease or condition (e.g., hyperinsulinemia, hyperglycemia, metabolic syndrome, Type 2 diabetes, Type 1 diabetes, and obesity) in a subject in need thereof, are provided by the disclosure and comprise administering to the subject a therapeutically effective amount of citrulline and a therapeutically effective amount of leucine (or a metabolite thereof) (e.g. hydroxy isocaproic acid (HICA) or beta-hydroxy-beta-methylbutyrate (HMB)). The inventors have unexpectedly found that citrulline and leucine (or a metabolite thereof) when administered to a subject reduces fasting plasma glucose levels and fasting plasma insulin levels below that achieved with administration of either citrulline or leucine alone (i.e., exhibits a synergistic effect). In some embodiments, the method is sufficient to achieve at least one of the following modifications: reduction in fasting blood sugar level, decrease in insulin resistance, reduction of hyperinsulinemia, and/or improvement in glucose tolerance. In some embodiments, the treatment or prevention method reduces a symptom of diabetes or the chances of developing a symptom of diabetes, wherein the symptom is selected from the group consisting of atherosclerosis, obesity, hypertension, hyperlipidemia, fatty liver disease, nephropathy, neuropathy, retinopathy, foot ulceration and cataracts, associated with diabetes. Optionally, administration of the therapeutically effective amount of citrulline and the therapeutically effective amount of leucine (or a metabolite thereof) results in an improvement in glycemic control in the subject.

The present disclosure also provides compositions (e.g., pharmaceutical compositions) that comprise citrulline and leucine (or a metabolite thereof) (e.g., hydroxy isocaproic acid (HICA) or beta-hydroxy-beta-methylbutyrate (HMB))

including, where citrulline and leucine (or a metabolite thereof) are present in a synergistic amount.

The present disclosure also provides nutritional supplements and medical foods that comprise citrulline and leucine (or a metabolite thereof) (e.g., hydroxy isocaproic acid (HICA) or beta-hydroxy-beta-methylbutyrate (HMB)) including, where citrulline and leucine (or a metabolite thereof) are present in a synergistic amount.

Citrulline and leucine (or a metabolite thereof) for use according to the present disclosure can be formulated in compositions, especially pharmaceutical compositions, for use in the methods herein. Such compositions comprise a therapeutically or prophylactically effective amount e.g., a synergistic amount) of citrulline and leucine (or a metabolite thereof) in admixture with a suitable carrier, e.g., a pharmaceutically acceptable agent.

Pharmaceutically acceptable agents include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with albumin are exemplary appropriate carriers. The pharmaceutical compositions can include antioxidants such as ascorbic acid; low molecular weight polypeptides; proteins, such as serum albumin, gelatin, or immunoglobulins; hydrophilic polymers such as polyvinylpyrrolidone; amino acids; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also can be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers can be conventional buffers such as acetate, borate, citrate, phosphate, bicarbonate, or Tris-HCl. Acetate buffer may be about 4-5.5, and Tris buffer can be about pH 7-8.5. Additional pharmaceutical agents are set forth in Remington's Pharmaceutical Sciences, 18th Edition, A. R. Gennaro, ed., Mack Publishing Company, 1990.

The composition can be in liquid form or in a lyophilized or freeze-dried form and may include one or more lyoprotectants, excipients, surfactants, high molecular weight structural additives and/or bulking agents (see for example U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g. polysorbate 20, polysorbate 80); poloxamers (e.g. poloxamer 188); polyethylene glycol) phenyl ethers (e.g. Triton); sodium dodecyl sulfate (SDS); sodium laurel sulfate; sodium octyl glycoside; laurel-, myristyl-, linoleyl-, or stearyl-sulfobetaine; lauryl-, myristyl-, linoleyl- or stearyl-sarcosine; myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl ofeyl-taurate; and the MONAQUAT® series (Mona Industries, Inc., Paterson, N.J.), polyethyl glycol, polypropyl glycol, and copolymers of ethylene and propylene glycol (e.g. Pluronics, PF68 etc). Exemplary amounts of surfactant that may be present in the pre-lyophilized formulation are from about 0.001-0.5%. High molecular weight structural additives (e.g. fillers, binders) may include for example, acacia, albumin, alginic acid, calcium phosphate (dibasic), cellulose, carboxymethylcellulose, carboxymethylcellulose sodium, hydroxyethylceltulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose; starch; and zein. Exemplary concentrations of high molecular weight structural additives are from 0.1% to 10% by weight. In other embodiments, a bulking agent (e.g., mannitol, glycine) may be included.

Compositions are suitable for administration to a subject by any route available to the skilled worker, such as intraarticular, subcutaneous, intravenous, intramuscular, intraperitoneal, intracerebral (intraparenchymal), intracerebroventricular, intramuscular, intraocular, intraarterial, intralesional, intrarectal, transdermal, oral; and inhaled routes. A parenteral formulation typically will be a sterile, pyrogen-free, isotonic aqueous solution, optionally containing pharmaceutically acceptable preservatives.

Suitable and/or preferred pharmaceutical formulations can be determined in view of the present disclosure and general knowledge of formulation technology, depending upon the intended route of administration, delivery format, and desired dosage. Regardless of the manner of administration, an effective dose can be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages can be ascertained through use of appropriate dose-response data.

The pharmaceutical compositions can comprise citrulline and leucine (or a metabolite thereof) in combination with other active agents. Such combinations are those useful for their intended purpose. The combinations which are part of this disclosure can be citrulline and leucine (or a metabolite thereof) and at least one additional agent selected from the lists below. The active agents set forth below are illustrative for purposes and not intended to be limited. The combination can also include more than one additional agent, e.g., two or three additional agents if the combination is such that the formed composition can perform its intended function.

The disclosure further contemplates that pharmaceutical compositions comprising one or more other active agents may be administered separately from citrulline and leucine (or a metabolite thereof), and such separate administrations may be performed at the same point or different points in time, such as for example the same or different days.

Alternatively or in addition, therapeutic treatment with at least one or more additional active agents may be used which may act via different modes of action: 1) sulfonylureas (e.g., chlorpropamide, tolazamide, acetohexamide, tolbutamide, glyburide, glimepiride, glipizide) and/or meglitinides (e.g., repaglinide, nateglinide) that essentially, stimulate insulin secretion; 2) biguanides (e.g., metformin) act by promoting glucose utilization; reducing hepatic glucose production and diminishing intestinal glucose output; 3) alpha-glucosidase inhibitors (e.g., acarbose, miglitol) slow down carbohydrate digestion and consequently absorption from the gut and reduce postprandial hyperglycemia; 4) thiazolidinediones (e.g., troglitazone, pioglitazone, rosiglitazone, glipizide, balaglitazone, rivoglitazone, netoglitazone, troglitazone, englitazone, AD 5075, T 174, YM 268, R 102380, NC 2100, NIP 223, NIP 221, MK 0767, ciglitazone, adaglitazone, CLX 0921, darglitazone, CP 92768, BM 152054) that enhance insulin action, thus promoting glucose utilization in peripheral tissues; 5) glucagon-like-peptides including DPP4 inhibitors (e.g., sitagliptin); and 6) insulin, which stimulates tissue glucose utilization and inhibits hepatic glucose output. Glucagon-like peptide-1 (GLP-1) and analogs, DPP-IV-resistant analogues (incretin mimetics), DPP-IV inhibitors, insulin, insulin analogues, PPAR gamma agonists, dual-acting PPAR agonists, GLP-1 agonists or analogues, PTP1B inhibitors, SGLT inhibitors, insulin secretagogues, RXR agonists, glycogen synthase kinase-3 inhibitors, insulin sensitizers, immune modulators, beta-3 adrenergic receptor agonists. Pan-PPAR agonists, 11beta-HSD1 inhibitors, amylin analogues, biguanides, alpha-glucosidase inhibitors; meglitinides, thiazolidinediones, sulfonylureas and the like also may be used as the other active agent(s) (see for example Nathan, 2006, N. Engl. J. Med. 355:2477-2480; Kahn et al., 2006, N. Engl. J. Med. 355:2427-2443). In yet another embodiment, the active agent may be an HMG Co-A reductase inhibitor (e.g., statins).

The pharmaceutical compositions used in the disclosure may include a therapeutically effective amount or a prophylactically effective amount of citrulline and leucine (or a metabolite thereof). A therapeutically effective amount refers to an amount effective, at dosages and for periods of time necessary, to achieve the desired therapeutic result. A therapeutically effective amount may vary according to factors such as the disease state, age, sex, and weight of the individual, and the ability to elicit a desired response in the individual. A therapeutically effective amount is also one in which any toxic or detrimental effects are outweighed by the therapeutically beneficial effects. A prophylactically effective amount refers to an amount effective, at dosages and for periods of time necessary, to achieve the desired prophylactic result.

The present disclosure also provides a nutritional composition or a medical food comprising citrulline and leucine (or a metabolite thereof). Such compositions and foods comprise a therapeutically or prophylactically effective amount (e.g., a synergistic amount) of citrulline and leucine (or a metabolite thereof). In an embodiment, the nutritional composition comprises at least about 0.01 g to about 0.3 g of citrulline and at least about 0.01 g to about 0.3 g of leucine (or a metabolite thereof).

The nutritional composition can contain a protein source. Any type of dietary protein may be used, provided that the minimum requirements for essential amino acid content are met. However, in an embodiment, more than 50% or more than 60% by weight of the protein source is whey (hence ensuring a best balanced amino-acid profile). Thus, protein sources based on whey, casein and mixtures thereof may be used as well as protein sources based on soy, pea, rice or potato (and not restricted to these ones). Regarding whey proteins; the protein source may be based on acid whey or sweet whey or mixtures thereof and may include alpha-lactalbumin and beta-lactoglobulin in whatever proportions are desired.

The nutritional composition can contain a carbohydrate source. Any carbohydrate source conventionally found in nutritional compositions such as lactose, saccharose, maltodextrin, starch and mixtures thereof, may be used, although the preferred source of carbohydrates is lactose.

In an embodiment, the nutritional composition further comprises fats, such as, for example, fish oils or nonmarine oils or medium chain triglyceride (MCT). Non-limiting examples of fish oils include docosahexaenoic acid ("DHA") and eicosapentaenoic acid ("EPA"). Alternatively or additionally, DHA and EPA may be present from a non-fish oil source, e.g., algae, modified plants, and the like.

In some embodiments, the nutritional composition further comprises antioxidants. Non-limiting examples of suitable antioxidants include substances that inhibit oxidation or reactions promoted by Reactive Oxygen Species ("ROS") and other radical and non-radical species and also include molecules capable of slowing or preventing the oxidation of other molecules. For example, in addition to the fiber blend, the nutritional composition can further comprise carotenoids, coenzyme Q10 ("CoQ10"), flavonoids, glutathione Goji (wolfberry), hesperidine, lactowolfberry, lignin, lutein, lycopene, polyphenols, selenium, vitamin A, vitamin $B_1$, vitamin $B_6$, vitamin $B_{12}$, vitamin C, vitamin D, vitamin E, zeaxanthin, or combinations thereof.

In some embodiments, the nutritional composition further comprises vitamins, minerals or combinations thereof. Vitamins include fat-soluble or water-soluble organic substances essential in minute amounts for normal growth and activity of the body. The vitamins used in the composition are obtained naturally from plant and animal foods or synthetically made and can include pro-vitamins, derivatives and analogs. Non-limiting examples of suitable vitamins include Vitamin A, Vitamin $B_1$ (thiamine), Vitamin $B_2$ (riboflavin), Vitamin $B_3$ (niacin or niacinamide), Vitamin $B_5$ (pantothenic acid), Vitamin $B_6$ (pyridoxine, pyridoxal, or pyridoxamine, or pyridoxine hydrochloride), Vitamin $B_7$ (biotin), Vitamin $B_9$ (folic acid), and Vitamin $B_{12}$ (various cobalamins; commonly cyanocobalamin in vitamin supplements), Vitamin C, Vitamin D, Vitamin E, Vitamin K, folic acid, biotin and combinations thereof. Non-limiting examples of suitable minerals include boron, calcium, chromium, copper, iodine, iron, magnesium, manganese, molybdenum, nickel, phosphorus, potassium, selenium, silicon, tin, vanadium, zinc and combinations thereof.

In an embodiment, the nutritional composition further comprises phytonutrients that are health-promoting compounds from plant sources. The phytonutrients that can be used in the nutritional compositions are any chemicals produced by a plant that impart one or more health benefits on the user. Non-limiting examples of suitable phytonutrients include phenolic compounds, terpenes, betalains, organosulfides, protein inhibitors, other organic acids and combinations thereof.

The nutritional composition may contain emulsifiers and stabilizers such as soy lecithin, citric acid esters of mono- and di-glycerides, and the like. Furthermore, the nutritional composition may optionally contain other substances which may have a beneficial effect such as lactoferrin, nucleotides, nucleosides, and the like.

In an embodiment, the nutritional compositions comprise a prebiotic in addition to the 2-fucosylated oligosaccharide. A prebiotic is a food substance that selectively promotes the growth of beneficial bacteria or inhibits the growth or mucosal adhesion of pathogenic bacteria in the intestines. They are not inactivated in the stomach and/or upper intestine or absorbed in the gastrointestinal tract of the person ingesting them, but they are fermented by the gastrointestinal microflora and/or by probiotics. Prebiotics are, for example, defined by Glenn Gibson et al., "Dietary Modulation of the Human Colonic Microbiota: Introducing the Concept of Prebiotics," J. Nutr., 125: 1401-1412 (1995).

Non-limiting examples of prebiotics include acacia gum, alpha glucan, arabinogalactans, beta glucan, dextrans, fructooligosaccharides (FOS), galactooligosaccharides (GOS), fucosyllactoses, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, or their hydrolysates, or combinations thereof. The milk oligosaccharides may be bovine's milk oligosaccharides (BMOs) and/or human milk oligosaccharides (HMOs).

The nutritional composition may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins or the like), adsorbents, carriers, fillers, co-compounds, dispersing agents, wetting agents; processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatin of any origin, vegetable gums, ligninsulfonate, talc, sugars, starch, gum arabic, vegetable oils, polyalkylene glycols, flavoring agents; preservatives, stabilizers, emulsifying agents, buffers, lubricants, colorants, wetting agents, fillers, and the like.

The nutritional composition can be added in a product acceptable to the consumer (who is a human or an animal), such as an ingestible carrier or support, respectively. Examples of such carriers or supports are a pharmaceutical or a food or a pet food composition. Non-limiting examples for such compositions are milk, yogurt, curd, cheese, fermented milks, milk based fermented products, fermented cereal based products, milk based powders, human milk, preterm formula, infant formula, oral supplement, and tube feeding.

Further, the nutritional composition may contain an organic or inorganic carrier material suitable for oral or enteral administration as well as vitamins, minerals trace elements and other micronutrients in accordance with the recommendations of government bodies such as the USRDA.

The nutritional composition may be prepared in liquid form. Water is the most common carrier for the components of the composition, but the composition can be provided in other liquids such as; for example, milk, fruit juice, coffee, tea or other beverages, when such compositions are orally administered. Water is typically used for enteral formulations.

The nutritional composition can be a dry powdered formulation. The powdered formulation can be made by combining dry powdered ingredients or can be made from a liquid nutritional composition by drying the liquid composition with one of the processes known in the art, including spray drying, freeze drying or other drying techniques, to produce a dry powdered composition. If desired, other nutritional components or compositions can be added to the liquid prior to drying to provide enhanced nutritional benefits to the powdered formulation. Such powdered formulations have a much greater shelf life and can be packaged for storage and transport for future use. At that time, the powdered formulations can be reconstituted with Water or other fluids and then administered to the individual orally or enterally. The powdered formulation can be packaged in various containers, including those for bulk provision of such powdered formulations for adding to a liquid in a glass, bottle or other fluid containing vessel, or a single serving can be provided with the powder present in a container to which water or other fluids can be added to form the liquid for oral or enteral administration.

In an embodiment, the nutritional composition is a complete nutrition product that contains sufficient types and levels of macronutrients (protein, fats and carbohydrates) and micronutrients to be sufficient as a sole source of nutrition for the animal to which the composition is administered. In another embodiment, the nutritional composition is an incomplete nutrition product that does not contain sufficient levels of macronutrients (protein, fats and carbohydrates) or micronutrients to be sufficient as a sole source of nutrition for the animal to which the composition is administered.

The present disclosure also provides methods for treating or preventing a condition selected from the group consisting of metabolic syndrome, obesity, insulin resistance syndrome, diabetes (both primary essential diabetes such as Type II Diabetes and secondary nonessential diabetes) in a subject in need or treatment or in a subject in need of prevention by, administering to the subject a synergistic amount of citrulline and leucine (or a metabolite thereof) (e.g., a composition comprising a synergistic amount of citrulline and leucine (or a metabolite thereof), or a nutritional supplement or medical food comprising a synergistic amount of citrulline and leucine (or a metabolite thereof)) effective to treat the condition. The methods of the disclosure may be effective to relieve a symptom of diabetes or the chance of developing a symptom of diabetes, such as atherosclerosis, hypertension, hyperlipidemia, fatty liver disease, nephropathy, neuropathy, retinopathy, foot ulceration and cataracts, each such symptom being associated with diabetes, can be reduced.

The synergistic amount of citrulline and leucine (or a metabolite thereof) can be administered by any conventional route of systemic administration. Preferably they are administered orally. Other routes of administration that can be used in accordance with this disclosure include rectally, parenterally, by injection (e.g.: intravenous, subcutaneous, intramuscular or intraperitoneal injection), or nasally.

In an embodiment, the synergistic amount of citrulline and leucine (or a metabolite thereof) is administered to a subject with at least one other medically accepted treatment (e.g., medication, drug, therapeutic, active agent) for the disease, condition or complication, in another embodiment, the at least one other medically accepted treatment for the disease, condition or complication is reduced or discontinued (e.g., when the subject is stable), while treatment with the synergistic amount of citrulline and leucine (or a metabolite thereof) is maintained at a constant dosing regimen. In another embodiment, the at least one other medically accepted treatment for the disease, condition or complication is reduced or discontinued (e.g., when the subject is stable), and treatment with the synergistic amount of citrulline and leucine (or a metabolite thereof) is reduced (e.g., lower dose, less frequent dosing, shorter treatment regimen). In another embodiment, the at least one other medically accepted treatment for the disease, condition or complication is reduced or discontinued (e.g., when the subject is stable), and treatment with the synergistic amount of citrulline and leucine (or a metabolite thereof) is increased (e.g., higher dose, more frequent dosing, longer treatment regimen). In yet another embodiment, the at least one other medically accepted treatment for the disease, condition or complication is maintained and treatment with the synergistic amount of citrulline and leucine (or a metabolite thereof) is reduced or discontinued (e.g., lower dose, less frequent dosing, shorter treatment regimen). In yet another embodiment, the at least one other medically accepted treatment for the disease, condition or complication and treatment with the synergistic amount of citrulline and leucine (or a metabolite thereof) are reduced or discontinued (e.g., lower dose, less frequent dosing, shorter treatment regimen). The one other medically accepted treatment may include administering at least one pharmaceutical composition comprising an active agent selected from the group consisting of: a sulfonylurea, a meglitinide, a biguanide, an alpha-glucosidase inhibitor, a thiazolidinedione, a DPP-IV inhibitor, a glucagon-like peptide (GLP)-1 analog, insulin, or a combination thereof.

The disclosure further contemplates that the synergistic amount of citrulline and leucine a metabolite thereof) used in accordance with the methods provided herein, may be administered in conjunction with more traditional treatment methods and pharmaceutical compositions (e.g., active agents). Such compositions, may include for example, DPP-IV inhibitors, insulin, insulin analogues, PPAR gamma agonists, dual-acting PPAR agonists, GLP-1 agonists or analogues, PTP1B inhibitors, SGLT inhibitors, insulin secretagogues, RXR agonists, glycogen synthase kinase-3 inhibitors, insulin sensitizers, immune modulators, beta-3 adrenergic receptor agonists, Pan-PPAR agonists, 11beta-HSDI inhibitors, amylin analogues, biguanides, alpha-glucosidase inhibitors, meglitinides, thiazolidinediones, sulfonylureas and the like (see, e.g., Nathan, 2006, N. Engl. J. Med. 355:2477-2480; Kahn et al., 2006, N. Engl. J. Med. 355:2427-2443). In certain embodiments, the synergistic amount of citrulline and leucine (or a metabolite thereof) used in accordance with the disclosure may prevent or delay the need for additional treatment methods or pharmaceutical compositions. In other embodiments, the synergistic amount of citrulline and leucine (or a metabolite thereof) may reduce the amount, frequency or duration of additional treatment methods or pharmaceutical compositions.

Methods of treating or preventing a disease or condition in accordance with the present disclosure may use a predetermined or "routine" schedule for administration of the synergistic amount of citrulline and leucine (or a metabolite thereof). As used herein a routine schedule refers to a predetermined designated period of time between dose administrations. The routine schedule may encompass periods of time which are identical or which differ in length, as long as the schedule is predetermined. Any particular combination would be covered by the routine schedule as long as it is determined ahead of time that the appropriate schedule involves administration on a certain day.

Alternatively, methods of treating or preventing a disease or condition in accordance with the present disclosure may use a schedule for administration of the synergistic amount of citrulline and leucine (or a metabolite thereof) that is based upon the presence of disease symptoms as a means to determine when to administer one or more subsequent doses. Similar, this approach may be used as a means to determine whether a subsequent dose should be increased or decreased, based upon the effect of a previous dose.

The compositions disclosed herein may be effective to improve glycemic control. Assessment of improvement in glycemic control may be assessed, for example, based on a change in hemoglobin Alc (HbAlc, see for example Reynolds et al., BMJ, 333(7568):586-589, 2006). Improvements (e.g., decrease) in HbAlc that are indicative of therapeutic efficacy may vary depending on the initial baseline measurement in a patient, with a larger decrease often corresponding to a higher initial baseline and a smaller decrease often corresponding to a lower initial baseline. In one aspect of the disclosure, the method should result in an HbAlc decrease of at least about 0.5% (e.g., at least about 0.5%, at least about 1%, at least about 1.5%, at least about 2%, at least about 2.5%, at least about 3%, at least about 3.5%, at least about 4% or more) compared with pre-dose levels.

One or more of the following secondary endpoints also may be determined in order to assess efficacy of the treatment, such as for example fasting blood sugar (e.g., glucose) levels (e.g., decrease to <130, <125, <120, <115, <110, <105, <100, alternatively decrease of >20%, >30%, >40%, >50%, >60%; >70%, >80%, >90%, >95% compared to pre-dose levels), 120 minute oral glucose tolerance test (OGTT) (e.g., <200, <190, <180, <170, <160, <150, <140), glucose/insulin C-peptide AUC (e.g., >25%, >50%, >60%, >70%, >80%, >90%, >100% increase from pre-treatment), reduction in diabetes medication (e.g., insulin, oral hypoglycemic agent), improvement in insulin sensitivity.

Similarly, assessment of efficacy for other diseases or conditions may use one or more of the aforementioned endpoints and/or others known in the art. For example; the effect on hyperglycemia can be assessed by measuring fasting blood sugar (i.e.; glucose) levels, the effect on hyperinsulinemia may be assessed by measuring insulin levels and/or C-peptide levels, and the effect on insulin resistance may be assessed by OGTT.

Similarly, subjects treated in accordance with the present disclosure may; experience a decrease in insulin resistance. Such decrease in insulin resistance may be measured by an improvement in a homeostasis model assessment (HOMA), an insulin tolerance test, an insulin suppression test, a steady-state plasma glucose method, or any of the other assay methods know in the art (see, e.g., Matthews et al., 1985, Diabetologia 28:412-419; Odegaard et al., 2007, Nature 447:1116-1121; Emoto et al., 1999, Diabetes Care 22:818-822). Other of the aforementioned measurements may be made using any of a variety of standard assays known in the art, for example assays published in Chemecky C C, Berger B J, eds. (2004). Laboratory Tests and Diagnostic Procedures, 4th ed. Philadelphia: Saunders; Fischbach F T, Dunning M B III, eds. (2004). Manual of Laboratory and Diagnostic Tests, 7th ed. Philadelphia: Lippincott Williams and Wilkins; Genest J, et al. (2003). Recommendations for the management of dyslipidemia and the prevention of cardiovascular disease: Summary of the 2003 update. Canadian Medical Association Journal, 169(9): 921-924. Handbook of Diagnostic Tests (2003). 3rd ed. Philadelphia: Lippincott Williams and Wilkins; and Pagana K D, Pagan, T J (2002), Mosby's Manual of Diagnostic and Laboratory Tests, 2nd ed. St. Louis: Mosby.

The present disclosure also provides methods for selling a product containing synergistic amount of citrulline and leucine (or a metabolite thereof) comprising the step of promoting that the synergistic amount of citrulline and leucine (or a metabolite thereof) improves reduces fasting plasma glucose levels, reduces fasting plasma insulin levels, and/or improves glycemic control in a human.

Promotion of the composition comprising citrulline and leucine (or a metabolite thereof) including, a synergistic amount of citrulline and leucine (or a metabolite thereof), may be made by advertising campaigns. These campaigns may consist of print, television, radio, and/or internet advertising. Additionally or alternatively, promotion of the composition comprising citrulline and leucine (or a metabolite thereof) may include placing advertisements about the composition comprising citrulline and leucine (or a metabolite thereof) in journals and/or direct sale calls to consumers. Such promotional efforts may be directed to health care providers, including physicians, nurses and/or hospitals. Additionally or alternatively, promotional efforts may be directed to patients, including patients with a disease or disorder that may be treated with the composition comprising citrulline and leucine (or a metabolite thereof). The step of promoting the composition comprising citrulline and leucine (or a metabolite thereof) may include promoting the benefits of a product including a composition comprising citrulline and leucine (or a metabolite thereof) comprising the step of stating that the composition comprising citrulline and leucine (or a metabolite thereof) can be used to treat a metabolic disease, hyperinsulinemia, or hyperglycemia.

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure

EXAMPLES

Example 1

Figure 2:
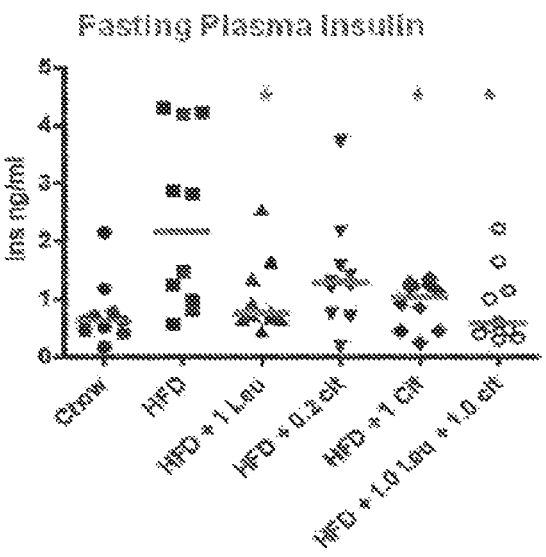
FIG. 2 shows fasting insulin plasma levels in rats fed a high fat diet (HFD) and treated with 0.2 or 1.0 g/kg/day of citrulline, 1.0 g/kg/day of leucine or 1.0 g/kg/day of both citrulline and leucine. P<0.05 versus HFD.

Administration of a Composition Comprising Citrulline and Leucine Reduces Fasting Glucose and Insulin Plasma Levels Compositions comprising citrulline, leucine, or citrulline or leucine were tested for their effect on fasting glucose levels and insulin plasma levels. Briefly, rats were split into six groups and fed either chow, a high fat diet, a high fat diet with 1 g/kg leucine daily, a high fat diet with 0.2 g/kg citrulline, a high fat diet with 1 g/kg citrulline daily or a high fat diet with a composition comprising 1.0 g/kg leucine and 1.0 g/kg citrulline. Rats fed a high fat diet and either 1 g/kg of citrulline or 1 g/kg leucine exhibited a decrease in fasting plasma glucose levels and insulin plasma levels as compared to rats fed a high fat diet. Only the administration of a composition comprising both citrulline and leucine achieved a significant result on glycemia. For plasma insulin level, citrulline alone or leucine alone were efficient but unexpectedly only the co administration of both leucine and citrulline allowed to completely normalised insulinemia at the level observed in healthy rats eating a standard chow diet, thus suggesting a synergic effect between citrulline and leucine (FIG. 1 and FIG. 2).

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using consisting of or and consisting essentially of language. When used in the claims, whether as filed or added per amendment, the transition term "consisting of excludes any element, step, or ingredient not specified in the claims. The transition term "consisting essentially of limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary, only, with the true scope and spirit of the disclosure being indicated by the following claims. All references, patents, and patent applications referred to in this application are herein incorporated by reference in their entirety.

The invention is claimed as follows:

1. A method of treating hyperglycemia in a subject in need thereof, the method comprising administering to the subject a therapeutically effective amount of citrulline and a therapeutically effective amount of leucine,
    wherein the subject is administered a weight-based dose of the citrulline and the leucine.

2. The method of claim 1, wherein the therapeutically effective amount of citrulline and the therapeutically effective amount of leucine result in a synergistic effect.

3. The method of claim 1, wherein the citrulline and the leucine are administered to the subject using a regimen selected from the group consisting of weekly, daily, two times a day, and three times a day.

4. The method of claim 1, wherein the subject is administered a fixed amount of the citrulline and the leucine.

5. The method of claim 1, wherein the weight-based dose is about 0.01 g/kg to about 0.3 g/kg of the citrulline and 0.01 g/kg to about 0.3 g/kg of the leucine.

6. The method of claim 1, wherein the weight-based dose is 1.0 g/kg of the citrulline and 1.0 g/kg of the leucine.

7. The method of claim 1, wherein a pharmaceutical composition is administered to the subject that comprises both the therapeutically effective amount of the citrulline and the therapeutically effective amount of the leucine.

8. The method of claim 1, wherein the therapeutically effective amount of the citrulline and the therapeutically effective amount of the leucine are administered orally.

9. The method of claim 1, wherein the subject is administered protein in conjunction with the citrulline and the leucine.

* * * * *